US009347916B2

(12) United States Patent
Moularat et al.

(10) Patent No.: US 9,347,916 B2

(45) **Date of Patent: *May 24, 2016**

(54) PROCESS FOR DETERMINING MYCOTOXIN PRODUCTION FROM A SPECIFIC CHEMICAL FINGERPRINT

(75) Inventors: Stéphane Moularat, Lognes (FR); Enric Robine, Lagny-sur-Marne (FR)

(73) Assignee: CENTRE SCIENTIFIQUE ET TECHNIQUE DU BATIMENT (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/607,307

(22) Filed: Sep. 7, 2012

(65) Prior Publication Data

US 2013/0244272 A1 Sep. 19, 2013

(30) Foreign Application Priority Data

Sep. 8, 2011 (FR) ..................................... 11 57992

(51) Int. Cl.

| | |
|---|---|
| ***C12Q 1/04*** | (2006.01) |
| ***G01N 27/62*** | (2006.01) |
| ***G01N 33/00*** | (2006.01) |
| ***G01N 33/543*** | (2006.01) |
| ***G01N 33/66*** | (2006.01) |
| *G01N 30/88* | (2006.01) |

(52) U.S. Cl.

CPC ............ *G01N 27/62* (2013.01); *G01N 33/0004* (2013.01); *G01N 33/54346* (2013.01); *G01N 33/54373* (2013.01); *G01N 33/66* (2013.01); *G01N 2030/8813* (2013.01); *G01N 2333/37* (2013.01)

(58) Field of Classification Search

USPC ........................................................... 435/34

See application file for complete search history.

(56) References Cited

U.S. PATENT DOCUMENTS

2010/0107740 A1* 5/2010 Moularat ..................... 73/31.03

OTHER PUBLICATIONS

Zeringue et al. C15H24 Volatile Compounds Unique to Aflatoxigenic Strains of Aspergillis Flavus; Applied and Environmental Microbiology, vol. 59, No. 7 (1993) pp. 2264-2270.*

Moulerat et al. Detection of Fungal Development in Closed Spaces Through the Determination of Specific Chemical Targets; Chemosphere, vol. 72 (2008) pp. 224-232.*

Chan et al. Determination of Organic Contaminants in Residential Indoor Air Using an Adsorption-Thermal Desorption Technique; The Journal of the Air and Waste Mangement Association, vol. 40 (1990) pp. 62-67.*

* cited by examiner

*Primary Examiner* — Paul Martin

(74) *Attorney, Agent, or Firm* — Amster, Rothstein & Ebenstein LLP

(57) ABSTRACT

The present invention relates to a process for determining mycotoxin production in an interior environment which includes a search for a chemical fingerprint comprising at least one target molecule that is a VOC, optionally cyclic, associated with mycotoxin production, preferably selected from the group comprising cububene, cadiene, copaene, ylangene, D germacrene, muurolane, 1,1-dimethylbutylbenzene, 1,1,2-trimethyl-propyl-benzene, 1-hexyltetradecylbenzene, tetratetracontane, 1-ethyldecylbenzene, hydroxytoluene butylate, 1-butyloctylbenzene, 1-propylnonylbenzene, 2-methylisoborneol and at least one sesquiterpene.

3 Claims, No Drawings

PROCESS FOR DETERMINING MYCOTOXIN PRODUCTION FROM A SPECIFIC CHEMICAL FINGERPRINT

TECHNICAL DOMAIN OF THE INVENTION

The present invention relates to a process for determining mycotoxin production in interior environments from a specific chemical fingerprint.

Interior environment is understood to mean a confined space inside a building which is not continuously ventilated. Examples of interior environments can be found in residences, museums, churches, caves, historic monuments, administrative buildings, schools and hospitals.

The WHO, in its report "WHO Guidelines for Indoor Air Quality: Dampness and Mould" (2009), reviews the now-recognized sanitary importance of microscopic fungi colonizing our habitats and especially their capacity to cause toxic pathologies linked to the mycotoxins which they produce. Also, the preventive detection of these undesirable biological entities is of increasing interest for the protection of occupants.

In this context, the fungal contamination index refined by the applicant and described in application WO 2008/125770 could be supplemented by early detection of mycotoxins.

STATE OF THE PRIOR ART

Thus, Zeringue et a in 1993 observed differences in VOC emissions between toxicogenic strains of *Aspergillus flavus* (producer of aflatoxins) and non-toxicogenic strains.

Desjardins determined in 1993 that volatile trichodiene is the first metabolite in the biosynthetic pathway of trichothecenes. This result was also found by Jelen et al. (1995; 1997a; 1997b) who established a correlation between the synthesis of trichothecenes and the production of trichodiene and other sesquiterpenes by *Fusarium sambucinum, F. sporotrichoides, F. poae* and *F. graminearum.*

Pasanen et al. (1996) indicated that the production of volatile terpenes and sesquiterpenes by *Fusarium* strains is associated with the production of trichothecenes.

The production of mycotoxins is only significantly detectable after an advanced fungal contamination, whereas one would like to avoid the generation of airborne mycotoxins. Furthermore detection of mycotoxins proves very difficult in comparison with detection of VOCs.

To overcome these disadvantages, a process is known from application WO 2008/125770 indicated above for detection of fungal contamination of an interior environment by means of calculating a fungal contamination chemical index. However, by implementing this process, specifically concluding whether or not there is production of mycotoxins is not possible.

DESCRIPTION OF THE INVENTION

In this context, it is particularly interesting to study the relationship between the VOC emissions and the toxicogenic nature of the fungal strain.

With the determination of a specific chemical fingerprint for the production of mycotoxins, it would then be possible to supplement the fungal contamination indices already developed by the applicant, by providing clear and precise criteria for decisions concerning the occupation and renovation of contaminated buildings.

Thus the applicant proposes a process for determining the production of mycotoxins in an interior environment comprising the steps of:

a) Collecting an air sample from the interior environment, and then b) Detecting VOCs in the sample.

According to a first aspect, step b) includes a search for a chemical fingerprint comprising at least one target molecule which is a VOC associated with mycotoxin production.

In particular, the target molecule is a cyclic VOC associated with mycotoxin production.

Particularly advantageously, the detection of such target molecules is easier and faster than the detection of mycotoxins.

Advantageously, said target molecule is selected from the group comprising cububene, cadiene, copaene, ylangene, D germacrene, muurolane, 1,1-dimethylbutylbenzene, 1,1,2-trimethyl-propyl-benzene, 1-hexyltetradecylbenzene, tetratetracontane, 1-ethyldecylbenzene, hydroxytoluene butylate, 1-butyloctylbenzene, 1-propylnonylbenzene, 2-methylisoborneol and at least one sesquiterpene.

According to a variant, the chemical fingerprint includes at least two target molecules of which at least one is a sesquiterpene.

Preferably, the chemical fingerprint includes all said target molecules.

According to an interesting variant, the process includes a step of searching for fungal contamination zones; this search is done before taking an air sample. Thus, in the case where fungal development is visible to the naked eye and forms a fungal contamination zone, the air sample can be taken from this contamination zone. A search for fungal contamination zones can also include microscopic analyses and microbiological or biochemical tests.

According to a second aspect, the process includes the steps of:

a) Collecting an air sample from the interior environment; and then b) Detecting VOCs in the sample, which includes detection of the presence or absence of certain set VOCs, coming from fungal metabolism where these set VOCs include at least one VOC from each of the following three categories of VOCs:

1) VOCs that are released independently of the fungal species and the medium thereof and which are released only by fungal species;

2) VOCs that are released independently of the fungal species and the medium, and which are released by non-fungal biological species;

3) VOCs that are released as a function of the fungal species and/or the medium thereof;

c) Calculating a fungal contamination chemical index as a function respectively of the presence and absence of the set VOCs coming from fungal metabolism.

"Medium" of a fungal species is understood to mean the material on which the fungal species develops, preferably a construction material such as wallpaper, fiberglass fabric or other.

Subsequently, the process includes a step d) of searching for a chemical fingerprint that includes at least one target molecule that is a VOC, associated with mycotoxin production.

The process according to the second aspect of the invention is particularly useful for the early detection of mycotoxin production, meaning before the appearance of detectable quantities of mycotoxins. This possibility of early detection is even more interesting because it does not require direct detection of mycotoxins. It can thus be concluded that mycotoxins are being produced at an early stage of development of the fungi. "Early stage" of development is understood to mean a stage where the fungi are invisible on the surface of the medium, and preferably undetectable by microbiological analysis of the air, but nonetheless producing metabolites and inhalable particles that are responsible in some circumstances for diseases.

DETAILED DESCRIPTION OF AN EMBODIMENT

A study of the VOC emissions from a strain of *Aspergillus versicolor* was conducted under different growth conditions:

Growth conditions allowing the production of sterigmatocystin, referred to as mycotoxin production conditions, and Growth conditions not allowing the production of sterigmatocystin, referred to as mycotoxin non-production conditions.

Samples of *Aspergillus versicolor* were cultured on fiberglass fabric and wallpaper. The culture was done on a nutrient medium with the following composition: for 1 liter of pH buffered solution (pH 7.4):

| | |
|---|---|
| $K_2HPO_4$: 1 g | $FeSO_4$; $7H_2O$: 0.01 g |
| KCl: 0.5 g | Glucose 31.5 g |
| $MgSO_4$; $7H_2O$: 0.5 g | $NaNO_3$: $3.5 \times 10^{-2}$ g |

The solution buffered to pH 7.4 is for example prepared with 250 mL of 0.1M $KH_2PO_4$ to which is added 145.5 mL of 0.1M NaOH; and the solution is topped off with 500 mL of distilled water.

After culture under mycotoxin production conditions, air samples were taken in both cases. No production of mycotoxins (notably sterigmatocystin) was detected in the test on the fiberglass fabric medium.

On the other hand, this study showed that on the wallpaper medium there was not only production of mycotoxins but also production of more than ten compounds (including sesquiterpenes) related to the complex metabolic pathways taken by mycotoxin production. These compounds can therefore be used as target molecules. Additional analyses of the wallpaper medium revealed that these compounds do not come from the wallpaper. This demonstrates that these compounds are directly related to the production of mycotoxins.

In particular the following target molecules were identified:

cububene, cadiene, copaene, ylangene, D germacrene, muurolane, 1,1-dimethylbutylbenzene, 1,1,2-trimethyl-propyl-benzene, 1-hexyltetradecylbenzene, tetratetracontane, 1-ethyldecylbenzene, hydroxytoluene butylate, 1-butyloctylbenzene, 1-propylnonylbenzene, 2-methylisoborneol and sesquiterpenes.

Other target molecules can be identified. Generally, target molecules of this type can consist of any compound related to the metabolic pathways taken by mycotoxin production, meaning compounds produced by the fungi during mycotoxin production. It emerges from the initial analyses that a large proportion of these compounds comprise rings (sometimes benzene rings). Additionally, most of these compounds have a molecular mass greater than 204.

Thus, a specific chemical fingerprint of the production of mycotoxins can be determined with which to supplement the fungal contamination indices already developed in application WO 2008/125770, by providing clear and reliable criteria for decisions concerning for example the occupation and renovation of contaminated buildings.

In the case of *Aspergillus versicolor*, one observed chemical fingerprint is constituted by the following target molecules: cububene, cadiene, copaene, ylangene, D germacrene, muurolane, 1,1-dimethylbutylbenzene, 1,1,2-trimethyl-propyl-benzene, 1-hexyltetradecylbenzene, tetratetracontane, 1-ethyldecylbenzene, hydroxytoluene butylate, 1-butyloctylbenzene, 1-propylnonylbenzene, 2-methylisoborneol and the sesquiterpenes.

From a practical perspective, after determination of the presence of fungal development by the fungal contamination index, the search for specific targets of mycotoxin production makes it possible to signal probable production of mycotoxins associated with this fungal development. The number of targets present is then linked to a probability of exposure to these metabolites.

In the implementation of the process according to a preferred variant, the following steps are done successively:

a) Collecting an air sample from the interior environment, for example near the areas suspected of being contaminated;

b) Detecting VOCs in the sample, which includes the detection of the presence or absence of certain set VOCs coming from fungal metabolism where these set VOCs include at least one VOC from each of the following three categories of VOCs:

1) VOCs that are released independently of the fungal species and the medium thereof and that are released only by fungal species;

2) VOCs that are released independently of the fungal species and the medium, but which can also have other biological origins VOC having "other biological origins" is understood in particular to mean VOCs released by non-fungal biological species;

3) VOCs that are released as a function of the fungal species and/or the medium thereof;

c) Calculating a fungal contamination chemical index as a function respectively of the presence and absence of the set VOCs coming from fungal metabolism, in accordance with the process described in application WO 2008/125770, for determining whether there is a fungal contamination;

For determining whether there is mycotoxin production, the following steps are done in addition:

d) Searching for at least one target molecule, coming from mycotoxin production, whose molecular mass is optionally greater than 200 g per mole, in particular at least one target molecule selected from the group including cububene, cadiene, copaene, ylangene, D germacrene, muurolane, 1,1-dimethylbutylbenzene, 1,1,2-trimethyl-propyl-benzene, 1-hexyltetradecylbenzene, tetratetracontane, 1-ethyldecylbenzene, hydroxytoluene butylate, 1-butyloctylbenzene, 1-propylnonylbenzene, 2-methylisoborneol and at least one sesquiterpene;

e) Searching for a chemical fingerprint comprising at least two of said target molecules.

In a way that is interesting, new and inventive, the results from steps d) and e) make it possible to precisely, clearly and reliably determine whether or not there is mycotoxin production.

This embodiment of course leads to more complete results than those from the prior art, in that it is possible to conclude not only that there is fungal contamination with no visible sign of fungal development, but additionally it is possible to determine precisely and reliably that there is mycotoxin production.

In another variant of the invention, zones of fungal contamination can also be sought and then an air sample taken near these fungal contamination areas before searching for the said target molecule(s) discussed above, Such a search for fungal contamination areas can be performed for example with the naked eye, by microscopic analysis or by microbiological or biochemical tests.

The air sample collection is for example performed by diffusive sampling on a Carbograph 4 type adsorbent solid. The detection is performed for example using gas phase chromatography with mass spectrometry (GC-MS). Other detection methods can be used.

Many combinations can be considered without going outside the scope of the invention; a person skilled in the art will know how to choose one or the other according to the implementation constraints that need to be met.

The invention claimed is:

1. Process for determining mycotoxin production in an interior environment comprising the steps of:

a) collecting an air sample from the interior environment by sampling over a solid absorbent, and then b) detecting volatile organic compounds (VOCs) in the sample at least by gas chromatography followed by mass spectrometry (GC/MS), wherein step b) includes a search for a chemical fingerprint comprising molecules which are a VOC associated with mycotoxin production, the molecules comprising all of ylangene, D germacrene, 1,1-dimethylbutylbenzene, 1,1,2-trimethyl-propyl-benzene, 1-hexyltetradecylbenzene, tetratetracontane, 1-ethyldecylbenzene, hydroxytoluene butylate, 1-butyloctylbenzene, 1-propylnonylbenzene, cubebene, cadinene, copaene, muurolane and 2-methylisoborneol.

2. Process according to claim 1, further comprising a step of searching for fungal contamination zones conducted before step (a).

3. Process for determining mycotoxin production in an interior environment, comprising the steps of:

a) collecting an air sample from the interior environment by sampling over a solid absorbent; and then b) detecting volatile organic compounds (VOCs) in the sample at least by gas chromatography followed by mass spectrometry (GC/MS), which includes detection of the presence or absence of certain set VOCs coming from fungal metabolism where these set VOCs include at least one VOC from each of the following three categories of VOCs:

1) VOCs that are released independently of the fungal species and the medium thereof and that are released only by fungal species;

2) VOCs that are released independently of the fungal species and the medium, and which are released by non-fungal biological species;

3) VOCs that are released as a function of the fungal species and/or the medium thereof;

c) calculating a fungal contamination chemical index as a function respectively of the presence and absence of the set VOCs coming from fungal metabolism, wherein the process includes a step (d) of searching for a chemical fingerprint which comprises molecules which are a VOC associated with mycotoxin production, wherein said molecules comprise all 1,1-dimethylbutylbenzene, 1,1,2-trimethyl-propyl-benzene, 1-hexyltetradecylbenzene, tetratetracontane, 1-ethyldecylbenzene, hydroxytoluene butylate, 1-butyloctylbenzene, 1-propylnonylbenzene, cubebene, cadinene, copaene, ylangene, D germacrene and 2 methylisoborneol.

* * * * *